United States Patent [19]

Siskin et al.

[11] Patent Number: 5,611,915
[45] Date of Patent: Mar. 18, 1997

[54] PROCESS FOR REMOVAL OF HETEROATOMS UNDER REDUCING CONDITIONS IN SUPERCRITICAL WATER

[75] Inventors: Michael Siskin, Morristown; David T. Ferrughelli, Flemington, both of N.J.; Alan R. Katritzky, Gainesville, Fla.; William N. Olmstead, Murray Hill, N.J.

[73] Assignee: Exxon Research and Engineering Company, Florham Park, N.J.

[21] Appl. No.: 583,692

[22] Filed: Jan. 5, 1996

Related U.S. Application Data

[63] Continuation of Ser. No. 212,607, Mar. 9, 1994, abandoned.

[51] Int. Cl.$^6$ .................................................. C10G 1/06
[52] U.S. Cl. ............................ 208/433; 208/407; 208/952
[58] Field of Search ................................ 208/952, 407, 208/433

[56] References Cited

U.S. PATENT DOCUMENTS

| | | | |
|---|---|---|---|
| 3,660,269 | 5/1972 | McCauley . | |
| 3,819,506 | 6/1974 | Seitzer . | |
| 3,850,738 | 11/1974 | Stewart, Jr. et al. | 208/952 |
| 3,948,754 | 4/1976 | McCullum et al. | 208/952 |
| 3,960,702 | 6/1976 | Allred | 208/952 |
| 4,005,005 | 1/1977 | McCullum et al. | 208/952 |
| 4,028,220 | 6/1977 | Urquhart | 208/952 |
| 4,036,731 | 7/1977 | Martin . | |
| 4,089,773 | 5/1978 | Espenscheid | 206/6 |
| 4,166,022 | 8/1979 | Tsai | 208/952 |
| 4,298,452 | 11/1981 | Dorawala | 206/828 |
| 4,443,321 | 4/1984 | Compton | 208/952 |
| 4,968,414 | 11/1990 | Delbianco | 208/414 |
| 5,128,017 | 7/1992 | Delbianco | 208/414 |
| 5,151,173 | 9/1992 | Vaughn | 208/430 |
| 5,269,947 | 12/1993 | Baskis | 210/774 |

FOREIGN PATENT DOCUMENTS

| | | |
|---|---|---|
| 2000251 | 4/1991 | Canada . |
| 1461280 | 1/1977 | United Kingdom . |
| 1489920 | 10/1977 | United Kingdom . |
| 2175599 | 12/1986 | United Kingdom . |

OTHER PUBLICATIONS

Supercritical Fluid Extract Appl. to Coal Liq. Chemical Engin. News Aug. 29, 1983.

Cummins, et al., Energy Communic., 6(2), pp. 117–135 (1980) "Conversion of Oil–Shale Kerogen in CO–Steam at Low Pressure".

Lim, et al., ACS Div. Fuel Chem. Prep. 38(3), 1014 (1993) "Param. Eval. of Low Temperature CO Pretreatment of Subbit. Coal".

EP Application No. 0,264,743 A2 publ. 27.04.88, Eniriceiche, S.p.A. "Proc. for Prep. of Syn. Fuel From Coal".

Siskin, et al., Science 254,231 (11 Oct. 1991) "Reactivity of Organic Compounds in Hot Water . . . ".

Siskin, et al., Tetrahedron Letters 34 (30), 4739 (1993), "Unprecedented Pyridine Ring C—C Bond Cleavages . . . ".

Siskin, et al., Energy & Fuels, 7 (1993) 589 A.C.S., "Aqueous Organic Chemistry 6 . . . ".

Katritzky, et al., Energy & Fuels, 4 (1990), 493 A.C.S., "Aqueous High Temperature Chemistry of Carbo–and Heterocycles 1 . . . ".

Siskin, et al., Energy & Fuels 4 (1990), 475 A.C.S., "Aqueous Organic Chemistry. 1 Aquathermolysis . . . ".

Katritzky, et al., Energy & Fuels 6 (1992), 43, A.C.S., "Aqueous High Temperature Chem. of Carbo–and Heterocycles 17 . . . ".

Stenberg, et al., J. Org. Chem. 43 (13) (1978), "Carbon Monoxide–Hydrogen–Water . . . ".

Baltisberger, et al., "Carbon Monoxide–Water vs. Hydrogen for Liquefaction . . . ".

Siskin, et al., E.P. Application No. 90310317.4 Publication No. 0419265A1, published Mar. 27, 1991.

*Primary Examiner*—Helane Myers
*Attorney, Agent, or Firm*—Linda M. Scuorzo

[57] ABSTRACT

A process for heteroatom removal-enhancing hydrogenation of highly refractory aromatic ring structures that involves contacting a highly refractory structure having at least one aryl linkage connecting a first heteroaryl moiety and a moiety selected from the group consisting of an aryl moiety and a second heteroaryl moiety with supercritical water having a temperature of from about 400° C. to about 600° C. in the presence of from about 3.4 MPa to about 18.6 MPa of CO to produce lower molecular weight products having decreased aromatic and heteroatom content. The process has utility for producing more valuable lower molecular weight products having a reduced aromatic heteroatom content from starting materials that are highly refractory and widely considered to be difficult to upgrade such as coals and asphaltenes, and model compounds containing the biaryl linkages.

9 Claims, No Drawings

PROCESS FOR REMOVAL OF HETEROATOMS UNDER REDUCING CONDITIONS IN SUPERCRITICAL WATER

This is application is a continuation of application U.S. Ser. No. 212,607, filed Mar. 9, 1994, now abandoned.

FIELD OF THE INVENTION

The invention relates to a process for aqueous heteroatom removal-enhancing hydrogenation of certain aromatic ring structures.

BACKGROUND

There is a paucity of literature on heteroatom removal-directed/enhancing aqueous CO hydrogenation of refractory heteroatom containing aromatic ring structures such as those typically found in coals and similar organic resources in the absence of certain reaction inducing factors such as transition metal catalysts. Stenberg, et al. *J. Am. Chem. Soc.* 43, 2991 (1978) teaches that quinoline can be hydrogenated using supercritical water and CO at 425° C., optionally in the presence of $Na_2CO_3$, but Stenberg's product analysis specifically shows that nitrogen was not removed. Appell, et al. *Prepr.-Pap. ACS Div. Fuel Chem.* 12, 220(1968) and Appell, et al., *Prepr.-Pap. ACS Div. Fuel Chem.* 13, 39 (1969) teach that a complex mix of products may be produced by treating a coal with CO and water in a conversion process at a temperature of below about 425° C. British Patent 1,461,280 to Bull, et al., suggests that sulfur can be removed under aqueous CO conditions in the presence of a hydrogenated aromatic solvent. Given the known stability of heteroatom containing biaryl linkages, one skilled in the art would not expect that the product mix would have been the result of dearomatization and cleavage of structures containing the biaryl bond.

To date only one publication, Siskin, *Tetrahedron Letters* 34, 4739 (1993), discloses hydrogenation along with heteroatom removal under aqueous CO reaction conditions, and that reference shows only that a monoaromatic heteroatom containing ring (i.e., pyridine) was reactive. No compounds containing biaryl linkages were tested nor did the reference suggest that they would be reactive.

There has been a measure of success, in liquid and supercritical water based systems, in reacting molecules containing certain linkages typically found in coal, such as ethers, sulfides and amines. See, e.g., Siskin in *Science* Vol. 254 p. 231–237, (11 Oct. 1991 ) which teaches that liquid water may be used under certain conditions. M. T. Klein, *Fuel* 64, 635 (1985); *Industrial Eng. Chem. Products Res. & Devel.* 24, 300 (1985); *Fuel Science and Technol.* 6, 633 (1988), teaches ethers, amines and sulfides may be cleaved in supercritical water. Hydrogenation and removal of nitrogen and sulfur from heteroaromatic rings is not taught or suggested. In addition, the molecules disclosed by Siskin and Klein contain linkages that are known to be much more reactive than those on which Applicant's process operates. Thus, one skilled in the art would not consider these disclosures to be relevant teachings.

Certain literature does describe processes that operate on organic resources, such as coal. For example, in U.S. Pat. No. 3,988,238 to McCollum, supercritical water may be used to crack and remove nitrogen and sulfur from coals. However, McCollum required the presence of a sulfur resistant transition metal catalyst and did not teach hydrogenation of the resource, given the absence of a reducing agent such as CO in the system. McCollum, U.S. Pat. No. 4,005,005 also suggests that tar sands may be cracked, and desulfurized using a dense fluid extraction. However, the patent specifically teaches that a reducing environment is not an element of the process. U.S. Pat. No. 5,269,947 to Baskis discloses a two zone water based thermal depolymerization process for process materials such as coal, with removal of some sulfur, but only by virtue of the inclusion of a separate catalytic sulfur removing process unit. Similarly Delbianco, U.S. Pat. No. 4,968,414 discloses a two stage process for coal liquefaction in the presence of CO and an alkaline carbonate or hydroxide. However, Applicants process operates without the required temperature staging of Delbianco.

Some processes do exist in which a reducing environment, specifically CO is disclosed. For example U.S. Pat. No. 5,151,173 to Vaughn discloses CO pressures of from about 800 to about 4500 psi, in conjunction with liquid water at a temperature of less than 700° F. for coal depolymerization and hydrogenation. The process, however, specifically teaches that heteroatom content reduction from coal does not occur (see e.g., Table 6 of U.S. Pat. No. 5,151,173). This is consistent with that which one skilled in the art would expect, given the highly aromatic content of coals. In addition, the work by Appell described previously, even though carried out at higher temperatures also did not teach that heteroatom removal may be accomplished.

Canadian Patent 2,000,251 to Berkowitz discloses a supercritical water CO extraction upgrading process for generating liquids from tar sands. However, there is no teaching nor suggestion of N or S removal, which is understandable given the nature (high H to C ratio) of the resource on which the process operates. Upgrading in this reference means making liquid products of an unspecified nature.

Finally, Cummins, *Energy Commun.*, 6,117 (1980), has reported the use of a CO-steam process to convert or crack oil shale kerogens to liquid products. However, he also reported that hydrogenation did not produce any nitrogen or sulfur removal within the temperature range of 300°–450° C., and specifically required a constant CO pressure of only 1.4 MPa (200 psig).

SUMMARY OF THE INVENTION

The present invention provides a process for heteroatom removal-enhancing or heteroatom decreasing hydrogenation of certain types of highly refractory heteroatom containing aromatic ring structures. These structures may be found in both molecules and in macromolecular structures such as coal. These highly refractory compounds, typically have a low H:C ratio, typically up to about 1.25, more typically up to about 1.00, most typically up to about 0.65 They are identified as having a linkage or bond connecting a heteroaryl moiety and a moiety selected from the group consisting of aryl and heteroaryl moieties. Such linkages are also often called "biaryl" or "biaromatic" linkages or bonds due to the presence of an aryl moiety on either side of the linkage. The terms are, therefore, used inter-changeably herein.

In the process of the present invention. The material containing such linkages is contacted with supercritical water, preferably above about 440° C. typically from about 440° C. to about 600° C., in the presence of CO in an amount effective to form an aqueous solution or mixture having a hydride ion species having sufficient concentration capable of transfering hydride ions to carry out an effective amount of hydrogenation, and reacting the solution or mixture for a time sufficient to enhance the hydrogenation of the heteroaryl moiety and the reactivity of the biaryl bonds to facilitate heteroatom removal or reduction. Such species are exemplified by formic acid and inorganic formates. This reaction is typically evidenced by the presence of lower molecular weight products having aromatic heteroatom-depleted hydrocarbon and de-aromatized ring structures, and ultimately, reduced or decreased heteroatom content of the product compared to the starting materials. In the ultimate end products the heteroatoms are typically released as ammonia, sulfur and hydrogen sulfide.

As concerns the portion of the starting material that reacts, the reaction products have an increased hydrogen content and decreased aromatic heteroatom content as compared to the starting material. Thus, the process has utility in producing higher value aromatic heteroatom-depleted lower molecular weight products, particularly liquids, from lower value materials.

The present invention may suitably comprise, consist or consist essentially of the elements or steps disclosed herein.

DETAILED DESCRIPTION OF THE INVENTION

Presently the only viable commercial process for utilizing coal is burning. It would be desirable to have alternative processes wherein this and similar highly aromatic heteroatom containing materials could have their reactivity toward aromatic ring heteroatom removal enhanced, and be converted to more valuable materials such as higher H:C ratio containing materials, lower molecular weight moieties or products and hydrocarbon liquids. Such processes typically would involve two major reactions (1) breaking crosslinks to depolymerize and (2) adding a source of hydrogen to increase the H:C atomic ratio and decrease aromaticity. The process of the present invention may be used to accomplish both. In addition, the process may be used to facilitate or enhance the removal of undesirable aromatic heteroatoms, specifically nitrogen and sulfur contained in heteroaromatic rings. Compounds containing aromatic carbon-aromatic carbon type crosslinks (i.e., biaryl bonds or linkages), in the form of aryl-heteroaryl and biheteroaryl structures are known in the art to be extremely refractory crosslinks due to the high bond energy of aromatic (aryl) carbon to carbon bonds. Applicants have found that under certain CO reducing conditions in supercritical water these structures can be hydrogenated preferentially at the heteroaromatic ring with subsequent dearomatization and reduction in heteroatom content.

This invention provides a process for activating or enhancing the reactivity of certain biaryl heteroatom containing species to facilitate the reduction or removal of heteroatoms selected from the group consisting of nitrogen and sulfur containing species from aryl-heteroaryl and heteroaryl-heteroaryl ("biheteroaryl") containing structures. In the process a molecule or macromolecular structure containing at least one (bi-)aryl linkage bonding or connecting an aryl to a heteroaryl moiety and a heteroaryl to a heteroaryl moiety is contacted with supercritical water in the presence of carbon monoxide and, optionally inorganic base, to effect preferential hydrogenation of the heteroatom-containing aromatic ring moiety. This facilitates enhanced hydrogenative heteroatom removal from compounds having a high degree of aromaticity and thus a lower H:C ratio. It may be accompanied by other depolymerization reactions of the molecular or macromolecular structure depending on the compound used as a starting material. Thus, the present invention provides a process for the hydrogenative reduction of the aromatic heteroatom content of highly refractory hydrocarbon containing structures. The process may be practiced on any moleculur structures or group of structures containing these types of aryl-heteroaryl and biheteroaryl linkages from small heteroatom containing biaryl molecules, e.g., bipyridyls, bithiyls, thiylpiridines, phenylpyridines, phenylthiophenes, to large macromolecular structures such as coals and asphaltenes. As used herein the term heteroatom means nitrogen and sulfur heteroatoms bonded in an aromatic ring to carbon atoms. Suitably the heteroaryl moieties may be either 5 or 6 member-carbon containing single (i.e., mononuclear) aromatic ring or polynuclear aromatic ring systems. In heteroaryl rings a heteroatom replaces at least one of the carbon atoms in the ring and the number of carbon atoms in the ring is reduced by an number equal to the number of heteroatoms in the ring. Typically, the number of carbon atoms in the heteroaryl ring is at least about 2 in a 5 membered ring or 3 in a 6 membered ring. However, the aromatic character or structure should be maintained in both the aryl and heteroaryl rings and the number of heteroatoms to carbon atoms will vary acordingly. Heteroaryl moieties may also contain nitrogen and sulfur either alone or in combination therein (i.e., heteroatoms that are the same or different).

It is evident that a number of combinations of 5 and 6 membered rings, both substituted and unsubstituted are possible when the heteroaryl or aryl moiety is a polynuclear aromatic ring system. Polynuclear aromatics may have any number greater than one 5 or 6 member ring and all such rings are fused. In coals, typically the polynuclear aromatics have predominantly up to 6 fused rings. However, the larger fused ring systems are not excluded from the process of the present invention.

The aryl-heteroaryl and the heteroaryl-heteroaryl moieties can be bonded to each other through any available aryl carbon-carbon bond. However, it is preferred if the aryl C-aryl C bond of at least one of the moieties is present in the heteroatom containing ring. Preferably the aryl-heteroaryl and biheteroaryl linkages are stabilized by the presence of fused aromatic rings on at least one side of the biaryl linkage. Thus, there have been no reports of enhancing the reactivity of materials containing aryl-heteroaryl or heteroaryl-heteroaryl linkages as taught by Applicants. The nature of any substitutents pendant from either the aryl or heteroaryl moiety will influence or limit the choice of available positions for bonding of the moieties as compared to the unsubstituted compounds.

As an additional benefit of the process of the present invention, the process also may be applied to cleave other bonds such as the C-S and C-O bonds as are found in diaryl sulfides and diaryl ethers and the like that are less refractory than biaryl bonds but are still widely considered too unreactive to cleave thermally.

It is known that organic resources such as higher rank coals and asphaltene fractions of heavy oils contain higher proportions of these more refractory crosslinks. Resource materials such as coals contain a variety of complex structures in addition to the heteroatom containing biaryls. Reactions using these resources as starting materials are known to produce a large number of end products, thus making it difficult, if not impossible to determine from analysis of the resource or of the liquid products which bonds were actually cleaved. In order to facilitate analysis model compounds representative of the structures and linkages of interest in the resource material are typically used. For this reason Applicants selected certain model compounds that reflect the likely composition, low H:C ratio, highly aromatic hydrocarbonaceous materials containing a heteroatom, such as in coals to assist in meaningfully interpreting the results. Otherwise, reaction results can be masked by complicated and in most cases incomplete product analysis.

All materials disclosed herein may be obtained from commercial sources or produced by known methods.

The process of the present invention may be carried out using any compound whether molecule or macromolecule having at least a first heteroaryl moiety wherein the first heteroaryl moiety is bonded or linked to an aryl or second heteroaryl moiety. The first heteroaryl moiety is bonded to the aryl or second heteroaryl group by an aromatic carbon-aromatic carbon bond (i.e., an aryl linkage). Thus, the process may be carried out on any compound having an aryl linkage connecting a heteroaryl moiety to an aryl or second heteroaryl moiety. An aryl-heteroaryl linkage is one in which the moiety on one side of the aromatic (i.e., aryl) carbon-carbon bond is an aromatic hydrocarbon moiety and on the other side a heteroaryl moiety (e.g., 2-phenylpyridine, 2-phenylindole, 2-naphthylbenzothiophene). A biheteroaryl linkage is one in which the moieties on either side of the carbon-carbon aromatic (i.e., aryl) bond are aromatic heterocycles (e.g., 2-(2-quinolyl)benzo[b]thiophene, 2-(2-thiyl-)benzo[b]thiophene, 2-2'-biquinolyl). Examples of such linkages may be represented by the formulas:

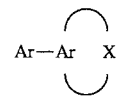 (1)

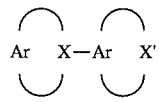 (2)

Ar is an aromatic or substituted aromatic hydrocarbyl (i.e., aryl or substituted aryl) moiety having at least one 5 or 6 membered carbon ring, wherein when the moiety has more than one ring the rings form a fused ring (i.e., polynuclear aromatic), and wherein X and X' each represent a heteroatom selected from the group consisting N and S which may be the same or different. In the above formulas, and throughout this description the two semicircular forms, represent heteroatom located in the aryl ring. An appropriate number of atoms may be bonded to the heteroatom as required to maintain the aromatic structure of the ring. For example, the heteroatom may be NH or S when the hydrocarbyl moiety is a 5 membered ring, and N, S or $S^+$ when the hydrocarbyl moiety is a 6 membered ring. It can be seen that in

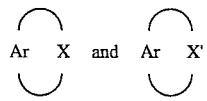

i.e., heteroatom containing rings, X and X' replace one of the carbon atoms in the 5 or 6 membered aromatic hydrocarbyl moiety. However, further replacements are not precluded.

Although the process of the present invention operates on other linkages herein it is required that the bond connecting the first heteroaryl moiety,

to the aromatic hydrocarbyl moiety, Ar, or second heteroaryl moiety,

be a biaryl bond. It is preferred that at least one heteroatom containing ring be located on the same ring as the biaryl bond.

In the process of the present invention the temperature is required to be above the critical temperature of water (374.4° C.). Temperatures above 600° C. tend to render the process uneconomical due to competing steam gasification reactions especially in the presence inorganic base, so typically temperatures of from about 440° C. to about 600° C. More preferably temperatures of from about 440° C. to about 550° C. most preferably from about 460° C. to about 550° C. may be used. Carbon monoxide should be introduced into the system in order to form and maintain a sufficient concentration of species capable of transferring hydride ions. In the system prior to heating to reaction temperature, CO pressures should be from about 500 psi (3.4 MPa) to about 2,700 psi (18.6 MPa), preferably 700 psi (4.8 MPa) to 1800 psi (12.4 MPa). Equivalent concentrations of formic acid, which thermally decomposes into CO and water, may be used for convenience. Inorganic hydroxide or carbonate base, preferably of Group IA and IIA metals and iron, nickel and aluminum, more preferably sodium may be added in stoichiometric or excess amounts to form inorganic formate, a prefered hydride ion donor (i.e., a quantitative or stoichiometric amount is based on the amount of CO present). An economical method of carrying out the process would also include adding the inorganic hydroxide or carbonate base in stoichiometric or excess concentration to the formic acid. Although the process may be used to effect the decrease in content and/or removal of both aromatic N and S, it is typically more effective in S removal in the presence of base. It is, therefore, desirable to add an inorganic base as described previously to the aqueous CO and resource mixture to enhance removal of S. In mixed N and S-containing feeds the choice to add optional inorganic base depends largely on the nature of the feed and process economics. Thus, as compared to processes known in the art the process of the present invention may be used to provide enhanced conversion of aryl-heteroaryl and biheteroaryl containing structures at the stated CO pressures (concentrations). Organic base may be used in combination with CO to produce the corresponding formate which results in a lower system pressure, and thus may be the economically more preferred route. In order to minimize undesirable side reactions, the process may be carried out using deoxygenated water. Additionally, with respect to coals it is known that oxidized coals give lower liquefaction yields, and for that reason it maybe economically less desirable to use oxygenated water. In the process the H:C ratio should be such that the starting material or reactant is highly aromatic and contains a large number of aryl linkages of the type described previously. Ratios of up to about 1.25, preferably up to about 1.0, or preferably up to 0.65 are suitable. The desired reactions typically may be obtained in high yields in as soon as about 1 hour at reaction conditions. When the reaction time is not of a sufficient duration to produce quantitative reaction the products nevertheless include aromatic heteroatom depleted products and hydrogenated species. As used -herein conversion means hydrogenation and effective cleavage of aryl-heteroaryl and biheteroaryl moieties accompanied by removal (ultimately as ammonia and hydrogen sulfide) of at least a portion of the aromatic heteroatoms, and includes hydrogenation that enhances the ability to remove heteroatoms under process conditions. It is generally evidenced by the formation of lower molecular weight liquid products and gases, typically aromatic hydrocarbons wherein heteroatoms are decreased or absent and wherein heteroaryl moieties are dearomatized. These liquid products are generally higher value added materials due to their suitability for use in other applications. Based on the unsubstituted molecules studied major liquid hydrocarbon products include benzene and naphthalene and their $C_1$ to $C_5$ alkylated derivatives. Benzenes, alkylbenzenes, naphthalenes, alkylnaphthalenes and similar aromatic hydrocarbons form a component of the liquid products produced in those cases in which the heteroaryl moieties contains more than one aromatic ring as a component of the liquid products that are produced. In cases in which the heteroaryl moiety contains only one aromatic ring but is bonded (through the biaryl bond) to an aryl moiety, aromatic hydrocarbon products can be produced. Biheteroaryl single ring systems will produce more aliphatic hydrocarbon products having reduced aromatic heteroatom content in comparison to the heteroaryl starting materials. For example, when the starting material contains an arylheteroaryl or biheteroaryl linkage the liquid end products will contain alkylaromatics as described previously. Thus, for example a benzothiophene group will produce largely ethylbenzene. Heteroaryl sulfur typically is largely removed as $H_2S$.

When the starting material is a low H:C ratio resource material such as coal the material should be crushed or otherwise reduced in particle size. Coals preferably in pieces of less than about 1.27 cm, more preferably less than about 0.64 cm or smaller may be used. For solid materials smaller particle sizes are more desirable. Water to starting material ratios of from about 10:1 to 1:1 preferably 5:1 to 1:1, more preferably about 2:1 to 1:1 are highly desirable. The operating parameters of temperature, pressure, residence or reaction time and in a continuous system flow velocity, may be balanced within the disclosed ranges to achieve the desired products.

EXAMPLES

General Procedure for Reactions:

All experiments were carried out in small (1.27 cm) stainless steel Swagelok (plug and cap), 1.7 mL capacity bombs which were not equipped for the collection or analysis of gaseous products. Distilled water, 15% aqueous formic acid, 15% or 30% aqueous sodium formate and cyclohexane were deoxygenated with argon for 1 hour just before use. The biheteroaryl or aryl-heteroaryl compound (0.16 g) and either deoxygenated cyclohexane, distilled water, 15% aqueous formic acid or 15% or 30% aqueous sodium formate (1.14 mL) were charged into the nitrogen blanketed stainless steel bomb, which was then sealed. The reactor was then placed, without agitation, in a Techne fluidized sandbath (model SBS-4) set at 460° C. using a Techne temperature controller (TC-8D) for a time period of 7 min., 1 hour or 2 hours (2 min heat-up time to 460° C.). After the reaction time period, the reaction was immediately quenched by cooling the bomb sequentially with cold air and dry ice, and the bomb was carefully opened while the contents were still solidified (at −78° C.) to vent carbon monoxide. The reaction mixture was then allowed to warm up to room temperature with periodic venting of gas. Distilled water and cyclohexane were used as controls to differentiate pure aqueous and thermal reactions, respectively, from the process using CO conditions.

The entire mixture was then transferred to a jar containing a Teflon stir bar. The walls of the reactor were rinsed with carbon tetrachloride or diethyl ether. This was added to the reaction mixture in the jar. After blanketing the jar with nitrogen and sealing it with a Teflon-lined cap, the entire mixture was stirred overnight at ambient temperature. Afterwards, the stirrer was stopped and the phases that developed were allowed to separate. The organic layer was pipetted from the aqueous layer and analyzed by gas chromatography and mass spectroscopy.

Analysis

All the GC analyses were carried out on a Hewlett Packard 5890 gas chromatograph operated in the split injection mode (30:1 ratio) and equipped with a flame-ionization detector (FID). A 15 m capillary column (SPB-1) was used and the oven temperature was programmed from 50°–250° C. with the initial time set at 1 min and a subsequent rate of 10° C./min. GC/MS analyses of all compounds were performed on a Varian 3400 gas chromatograph and a Finnigan MAT 700 ion trap detector.

Table I shows the results of the process, as a percent conversion of the starting materials to products. Major component hydrocarbon products are indicated in a separate column in the Table. The present invention is illustrated using a variety of aryl-heteroaryl containing starting materials, in 15% HCOOH, 15% $HCOON_a$ and 30% HCOONa at 460° C.

TABLE I

| | | | | 460° C., 1 Hour (% Conversion) | | | |
|---|---|---|---|---|---|---|---|
| Starting Compound | H:C Ratio | 15% HCOOH | % N or S Removed | Major Hydrocarbon Products | 15% HCOONa | % N or S Removed | Major Hydrocarbon Products |
| 2-PhPy | 1.00 | 56.5,(67.5)[a] | 99 | Benzenes(29%),(49%)[a] Naphthalenes(7%),(2,5%)[a] | 16.2 | 100 | Benzenes(11%) Naphthalenes(0.5%) |
| 2-NpPy | 0.73 | 66.9 | 98 | Naphthalenes(50%) Phenanthrenes(4%) | 22.7 | 91 | Benzenes(15%) |

TABLE I-continued

460° C., 1 Hour (% Conversion)

| Starting Compound | H:C Ratio | 15% HCOOH | % N or S Removed | Major Hydrocarbon Products | 15% HCOONa | % N or S Removed | Major Hydrocarbon Products |
|---|---|---|---|---|---|---|---|
| 2-PhQ | 0.77 | 61.0 | 41 | Benzenes(8%) | 15.6 | 37 | Benzenes(1.7%) Naphthalene(0.4%) |
| 2-NpQ | 0.68 | 87.8 | 70 | Benzenes(0.5%) Naphthalenes(45%) | 47.7 | 54 | Benzenes(13%) Naphthalenes(2%) |
| 2-PhIn | 0.71 | 18.7 | 74 | Benzenes(5%) | 3.9 | 36 | Benzenes(0.2%) |
| 2-NpIn | 0.72 | 38.0 | ≃58 | Benzenes(0.3%) Naphthalenes(13%) | 20.0 | ≃25 | Benzenes(0.1%) Naphthalenes(4%) |
| 2-PhT | 0.80 | 15.1 | 100 | Benzenes(4%) | 56.8,(99.4)$^a$ | 100,(100)$^a$ | Benzenes(41%),(87%)$^a$ Naphthalene(5%),(65%)$^a$ |
| 2-NpT | 0.71 | 23.9 | 100 | Naphthalenes(11%) Phenanthrenes(5%) | 82.7 | 100 | Naphthalenes(64%) Phenanthrenes(10%) |
| 2-NpBT | 0.71 | 24.3 | 90 | Benzenes(2%) Naphthalenes(9%) | 79.3,(98.2)$^b$ | >70,(90%)$^b$ | Benzenes(13%),(31%)$^b$ Naphthalenes(44%),(46%)$^b$ |

Legend:
Py = pyridine; Q = quinoline; In = indole; T = thiophene; Bt = benzothiophene; Ph = phenyl; Np = naphthyl.
Benzenes include benzene and $C_1$–$C_5$ alkylbenzenes, Naphthalenes include Naphthalene and $C_1$–$C_5$ alkylnaphthalenes
$^a$2 hours reaction time
$^b$30% sodium formate
Note: Formic acid, which decomposes thermally to water and CO, was used for convenience instead of CO.

What is claimed is:

1. A process for enhancing the reactivity of highly refractory heteroatom-containing aromatic ring structures, to facilitate heteroatom removal, consisting essentially of:

contacting a compound having at least one bond connecting a first heteroaryl moiety to a moiety selected from the group consisting of an aryl moiety and a second heteroaryl moiety, with supercritical water having a temperature of from about 440° C. to about 600° C. and from about 3.4 MPa to about 18.6 MPa of CO to produce lower molecular weight products having decreased aromatic heteroatom content.

2. The process of claim 1 wherein the biaryl-containing structure is present in a compound having an H:C ratio of up to about 1.25.

3. The process of claim 1 wherein the biaryl-containing structure is present in a compound having an H:C ratio of up to about 1.0.

4. The process of claim 1 wherein the structure is contained in a material selected from the group consisting of coals and asphaltenes.

5. The process of claim 1 wherein the structure is contained in a compound selected from the group consisting of 2-phenylpyridine, 2-naphthylpyridine, 2-phenylquinoline, 2-naphthylquinoline, 2-phenylindole, 2-naphthylindole, 2-phenylthiophene, 2-naphthylthiophene, 2-naphthylbenzothiophene.

6. The process of claim 1 wherein the temperature is from about 440° C. to about 550° C.

7. The process of claim 1 wherein CO is reacted to form a species capable of transferring hydride ions to the biaryl-containing structure.

8. A process for enhancing the reactivity of highly refractory heteroatom-containing aromatic ring structures, consisting essentially of:

contacting a compound having at least one bond connecting a first heteroaryl moiety to a moiety selected from the group consisting of an aryl moiety and a second heteroaryl moiety, with supercritical water having a temperature of from about 440° C. to about 600° C., CO at a pressure of from about 3.4 MPa to about 18.6 MPa, and an inorganic hydroxide or carbonate base, selected from the group consisting of Group IA and IIA metals, iron, nickel and aluminum to produce lower molecular weight products having decreased aromatic heteroatom content.

9. A process for enhancing the reactivity of highly refractory heteroatom-containing aromatic ring structures, consisting essentially of:

contacting a compound having at least one bond connecting a first heteroaryl moiety to a moiety selected from the group consisting of an aryl moiety and a second heteroaryl moiety selected from the group consisting of an aryl moiety and a second heteroaryl moiety, with supercritical water having a temperature of from about 40° C. to about 600° C., HCOOH sufficient to decompose generate CO at a pressure of from about 3.4 MPa to about 18.6 MPa, and an inorganic hydroxide or carbonate base selected from the group consisting of Group IA and IIA metals, iron, nickel and aluminum to produce lower molecular weight products having decreased aromatic heteroatom content.

* * * * *